United States Patent [19]
Bastable

[11] Patent Number: 5,910,110
[45] Date of Patent: Jun. 8, 1999

[54] CONTROLLING PRESSURE IN THE EYE DURING SURGERY

[75] Inventor: David Bastable, Norwell, Mass.

[73] Assignee: Mentor Ophthalmics, Inc., Norwell, Mass.

[21] Appl. No.: 08/472,884

[22] Filed: Jun. 7, 1995

[51] Int. Cl.$^6$ ....................................................... A61B 3/16
[52] U.S. Cl. ............................................................ 600/398
[58] Field of Search ................................... 128/645, 646, 128/898; 604/19, 21, 22, 35, 65, 67, 118, 119; 600/398, 399

[56] References Cited

U.S. PATENT DOCUMENTS

| | | |
|---|---|---|
| 3,659,607 | 5/1972 | Banko . |
| 3,693,613 | 9/1972 | Kelman . |
| 3,732,858 | 5/1973 | Banko . |
| 3,901,231 | 8/1975 | Olson . |
| 4,016,882 | 4/1977 | Broadwin et al. . |
| 4,168,707 | 9/1979 | Douvas et al. . |
| 4,184,510 | 1/1980 | Murry et al. ............................. 137/565 |
| 4,190,059 | 2/1980 | Holt . |
| 4,227,420 | 10/1980 | Lamadrid . |
| 4,315,520 | 2/1982 | Atkinson et al. . |
| 4,395,258 | 7/1983 | Wang et al. ......................... 604/119 X |
| 4,428,748 | 1/1984 | Peyman et al. . |
| 4,517,963 | 5/1985 | Michel . |
| 4,705,500 | 11/1987 | Reimels et al. . |

(List continued on next page.)

FOREIGN PATENT DOCUMENTS

| | | |
|---|---|---|
| 0-095-926 | 12/1983 | European Pat. Off. . |
| 0 180 317 | 5/1986 | European Pat. Off. . |
| 0 559 602 A2 | 9/1993 | European Pat. Off. . |
| 35-39-955 | 5/1987 | Germany . |
| 2132893 | 7/1984 | United Kingdom . |
| WO 93/24082 | 12/1993 | WIPO . |
| WO 93/24817 | 12/1993 | WIPO . |

OTHER PUBLICATIONS

Alcon® Surgical, Inc., "Series Ten Thousand Master Cataract System" advertisement, Fort Worth, Texas, 1989, two pages.

Dutch Ophthalmic Research Center bv, "Harmony Micro Surgical System for Anterior and Posterior Segment Surgery" brochure, Holland, Nov., 1990, eight pages.

Staar® Surgical Company, "Phaco XL™" instrument advertisement, Monrovia, California, Dec., 1991, one page.

Allergan Medical Optics, "Man and His Machines. The Perfect Partnership" PhacoPlus® brochure, Irvine, CA, 1990, seven pages.

United Surgical, "Incisions that Start Small Should Stay Small" PhacoMates$^{SM}$ brochure, Irvine, California, 1989, four pages.

site Microsurgical, "Site TXR® Is Your Total Surgical Phaco System" advertisement, Horsham, Pennsylvania, Nov., 1990, four pages.

Surgical Design Corporation, "Surgical Design Ocusystem II" brochure, New York, New York, Nov., 1990, four pages.

Mentor O&O, Inc., "Phaco made simple" brochure, Norwell, MA, 1991, three pages.

Harry G. Reimels, U.S. Serial No. 08/307,027, filed Sep. 15, 1994 (pending).

*Primary Examiner*—John P. Lacyk
*Assistant Examiner*—Samuel Gilbert
*Attorney, Agent, or Firm*—Fish & Richardson, P.C.

[57] ABSTRACT

Fluid pressure in the eye is monitored by detecting vacuum-induced deflections of a diaphragm on a reservoir that forms an integral part of the tube set through which fluid is supplied to and withdrawn from the eye. The rate at which fluid is withdrawn (i.e., aspirated) from the eye is controlled based on the detected deflections of the diaphragm. As a result, the detection component (e.g., a pressure sensor) is isolated from the fluids in the tube set by the diaphragm. This minimizes both the risk of contaminating the sensor with fluid aspirated from the patient, and the danger of so-called "cross-contamination" in which subsequent patients are exposed to the aspirated fluid of a prior patient.

18 Claims, 4 Drawing Sheets

U.S. PATENT DOCUMENTS

| | | |
|---|---|---|
| 4,757,814 | 7/1988 | Wang et al. . |
| 4,764,165 | 8/1988 | Reimels et al. . |
| 4,817,599 | 4/1989 | Drews . |
| 4,921,477 | 5/1990 | Davis .................................. 604/119 X |
| 4,993,265 | 2/1991 | Koen et al. . |
| 5,026,387 | 6/1991 | Thomas . |
| 5,053,002 | 10/1991 | Barlow . |
| 5,157,603 | 10/1992 | Scheller et al. . |
| 5,188,102 | 2/1993 | Idemoto et al. . |
| 5,209,719 | 5/1993 | Baruch et al. . |
| 5,211,625 | 5/1993 | Sakurai et al. . |
| 5,242,404 | 9/1993 | Conley et al. ........................... 604/119 |
| 5,335,551 | 8/1994 | Ohnishi et al. ..................... 128/672 X |
| 5,372,709 | 12/1994 | Hood . |
| 5,520,652 | 5/1996 | Peterson .................................. 604/119 |

CONTROLLING PRESSURE IN THE EYE DURING SURGERY

BACKGROUND OF THE INVENTION

This invention relates to monitoring and controlling the pressure of fluid in the eye during eye surgery.

The anterior region of the eye is a small, fluid-filled chamber. During surgery, fluid balance in the eye is maintained by supplying irrigation fluid to the eye and aspirating fluid from the eye using a surgical instrument. One such instrument, particularly useful in removing cataracts, is a phaco-emulsification instrument, which includes an ultrasonically vibrated hypodermic needle inserted into an incision in the eye to break up the cataract lens. The lens fragments and aspirated fluid are removed by suction through the needle. Typically, the surgical instrument is connected to the source of irrigation fluid and a drainage bag with a tube set that includes a series of individual, interconnected irrigation and aspiration tubes. After the procedure has been completed, the tube set is disassembled, and is either sterilized and reused or replaced with a new set of tubes for the next procedure.

To avoid damaging the eye, the rate at which irrigating fluid is supplied to the eye and aspirated (generally by inducing a vacuum in the aspiration tube using, e.g., a peristaltic pump) is controlled to ensure that the intraocular pressure remains within acceptable limits. Typically, such control is achieved by monitoring the vacuum in the aspiration tube with an electronic sensor connected to a branch of the aspiration tube. The rate at which fluid is supplied to the eye and/or aspirated from the eye is controlled based on the vacuum in the branch as measured by the sensor.

SUMMARY OF THE INVENTION

This invention features managing fluid flow in the eye during surgery by detecting vacuum-induced deflections in the tube set itself, and controlling the fluid flow rate based on the detected deflections. As a result, the detection component (e.g., a vacuum sensor) is isolated from the fluids in the tube set. This minimizes both the risk of contaminating the sensor with fluid aspirated from the patient, and the danger of so-called "cross-contamination" in which subsequent patients are exposed to the aspirated fluid of a prior patient.

In one general aspect of the invention, a portion of the tube set through which fluid is supplied to and withdrawn from the eye is constructed to deflect in a selected manner in response to the vacuum level in the tube set, and the rate at which fluid is withdrawn from the eye is controlled based on signals produced by a sensor positioned to detect the deflections.

Preferred embodiments include the following features.

The tube set includes a fluid reservoir, and the deflecting portion of the tube set is a diaphragm disposed on the reservoir. The reservoir and diaphragm are configured so that the diaphragm surface that is exposed to fluid contacts the fluid over substantially all of its area, and the reservoir is configured to be substantially filled with fluid from the tube set. As a result, even small vacuum changes are rapidly and accurately conveyed through the diaphragm to the sensor. Accordingly, the response time of the system components that control fluid aspiration is reduced, and the fluid flow rate through the eye is more accurately maintained within the required range.

Preferably, the tube set and the reservoir are constructed as an integral unit from a single piece of material. The tube set may be disposable (in which case, the material is, e.g., plastic) or reusable (and made from a material such as silicone rubber).

The thickness of the diaphragm is selected so that the diaphragm deflects in the selected manner in response to vacuum levels in the tube set. For example, the deflection response is linear with respect to pressure changes. Preferably, the diaphragm thickness is in the range of 0.005 inches to 0.006 inches. The diaphragm is made from silicone rubber.

The controller responds to the signals from the sensor by adjusting the speed of a pump that is disposed to engage the tube set to withdraw the fluid from the eye. The pump is preferably peristaltic.

In another aspect of the invention, the tube set and its fluid reservoir and diaphragm are received by a housing, and the deflection sensor is mounted on the housing adjacent to the diaphragm.

Preferred embodiments include the following features.

The housing includes a recess configured to receive the reservoir, and a mechanism for urging the reservoir into the recess to seal the diaphragm against a surface of the recess adjacent to the sensor. The sensor and the diaphragm are disposed adjacent to opposite sides of the surface, and the surface includes an opening between opposite sides.

The sealed interface between the diaphragm and the sensor efficiently transfers the vacuum-induced deflections of the diaphragm to the sensor. As a result, accuracy and response time are not compromised by the isolation between the fluids and the sensor that the diaphragm provides.

The housing includes a door movable between an open position, which allows the tube set to be installed in and removed from the housing, and a closed position in which the tube set is retained in the housing. A spring-biased plunger in the housing urges the reservoir into the recess (and seals the diaphragm against the recessed surface) when the door is closed. Closing the door also causes a section of the tube set to be urged against the peristaltic pump; the section of tube is released from the pump when the door is moved to the open position.

In yet another aspect of the invention, the tube set—including at least the portions through which irrigating fluid is supplied to and withdrawn from the eye and the reservoir—are constructed as an integral unit from a single piece of material.

Providing the reservoir as an integral part of the tube set dramatically simplifies the procedure for setting up the surgical system for use and, after surgery, for preparing the system for use with a subsequent patient. The tube set with its reservoir is installed into and removed from the housing as a unit. There is no need to assemble the various portions of the tube set during set-up, or disassemble the tube set after use.

In preferred embodiments, the tube set is formed by injection molding, and the diaphragm is then attached to the reservoir. A branch of the tube set interconnects the supply and withdrawal portions of the tube set.

Other features and advantages of the invention will become apparent from the following detailed description, and from the claims.

DESCRIPTION OF A PREFERRED EMBODIMENT

Figure 1:
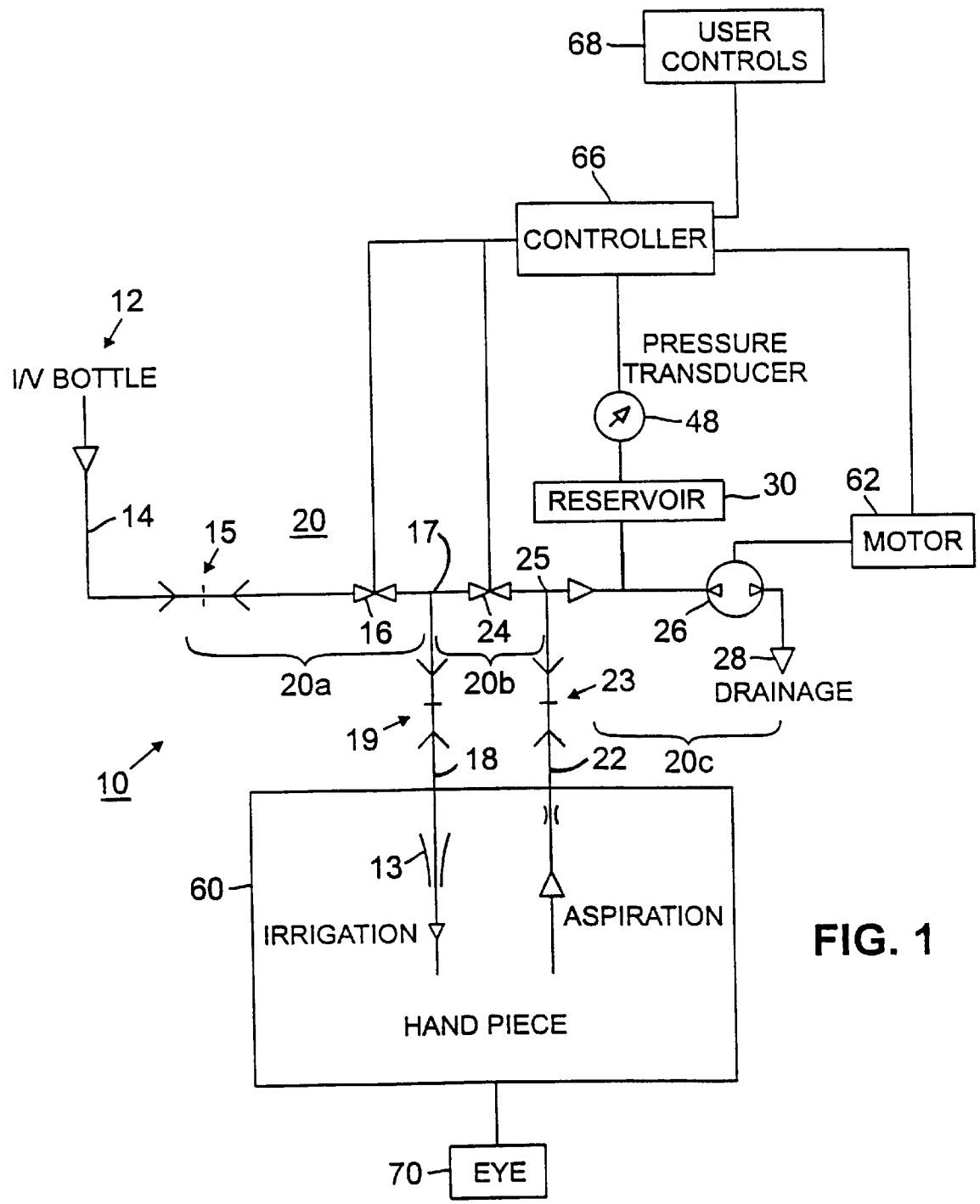
FIG. 1 schematically shows an eye surgery system.

FIG. 1 shows a system 10 for supplying fluids to and withdrawing fluids from the eye during eye surgery, and for monitoring and controlling the fluid flow rate. An IV bottle 12 supplies fresh fluid to a tube set 20 through a spike line 14 inserted into a female luer 15 of tube set 20. The fluid pressure at the input to tube set 20 is determined by the height of the IV bottle above the patient's eye (typically 60 cm). Fluid flows into tube set 20 when a pinch valve 16 is opened by the user, as discussed below.

Irrigation and aspiration tubes 18 and 22 are attached to tube set 20 at female luers 19 and 23, respectively. More specifically, luer 19 is connected to tube set 20 at fitting 17, which also provides a series connection between luer 15 and a similar fitting 25 that receives luer 23. Tube set branches 20a, 20b are acted upon by pinch valves 16, 24 for purposes to be described.

The distal ends of irrigation and aspiration tubes 18 and 22 are inserted into a handpiece 60, including a hydraulic nozzle 13, of a surgical instrument such as a phaco-emulsification unit for manipulation in eye 70.

A peristaltic pump 26 driven by motor 62 induces a vacuum in tube set 20 by alternately contracting and releasing a section 20c of tube set 20. This vacuum draws aspirated fluid from eye 70, through aspiration tube 22 and branch 20c, for disposal into a waste collection container (not shown) via a separate tube connected to tube set 20 at male luer 28.

The operation of motor 62 (and hence of pump 26) and pinch valves 16, 24 is managed by a controller 66, which in turn responds to user controls 68, as described in detail below. Among other parameters, user controls 68 include settings for a range of fluid flow rates and a maximum vacuum level in tube set 20. Controller 66 includes a programmed microprocessor (not separately shown) which responds to user controls 68, as well as the vacuum level in tube set 20 as measured by transducer 48 (described below), by adjusting the speed of motor 62 (and pump 26) to maintain the flow rate within the range set by the user and to avoid the vacuum level in tube set 20 exceeding the maximum set by the user. If necessary, controller 66 also closes pinch valve 16 (to stop further flow of irrigation fluid), opens pinch valve 24 (to reduce the vacuum level in tube set 20 to zero), and/or stops pump 26 to keep the flow rate within the selected range and prevent the maximum vacuum level from being exceeded.

Figure 2:
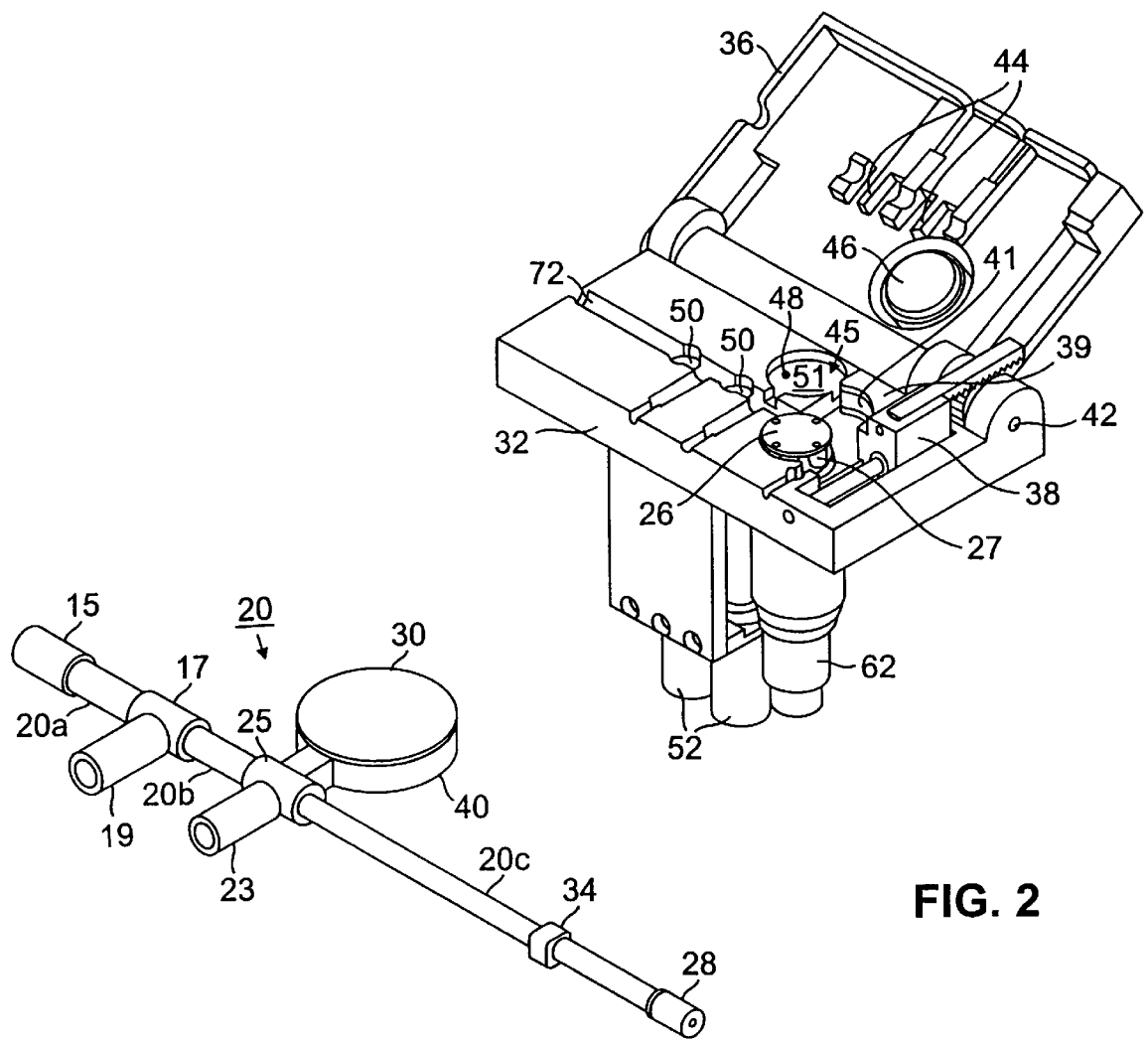
FIG. 2 illustrates two components of the system of FIG. 1: a tube set and a housing (shown in the open position) which receives the tube set.
Figure 3:
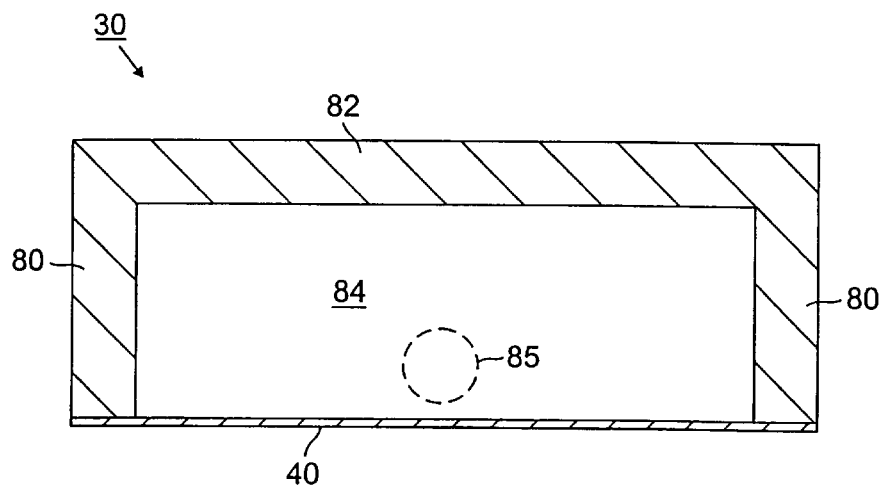
FIG. 3 is a cross-section of a fluid reservoir of the tube set of FIG. 2.

Referring also to FIGS. 2 and 3, transducer 48 measures the vacuum level by sensing vacuum-induced strain on a diaphragm 40 of a sealed, cylindrical reservoir 30 that forms part of tube set 20. Specifically, reservoir 30 is connected to the remainder of tube set 20 at fitting 25 (which includes a port 85 for admitting fluid into reservoir 30). Reservoir 30 thus is in the path of fluid aspirated from eye 70.

The lower wall (FIG. 3) of reservoir 30 comprises a thin (relative to the other walls of reservoir 30), circular diaphragm 40, which is tightly stretched over and rigidly attached to the lower surface of reservoir side walls 80 to form (with upper wall 82) a chamber 84. Fluid enters chamber 84 through port 85 in fitting 25. The thickness, diameter and material (e.g., silicone rubber) of diaphragm 40 is selected so that diaphragm 40 expands and contracts in a well-defined manner (described below) in response to vacuum-level changes within chamber 84. For example, diaphragm 30 is between 0.005 inch thick and 0.006 inch thick. In general, to use a thicker or thinner diaphragm 40, the diameter of diaphragm 40 must be larger or smaller, respectively. Transducer 48 detects the vacuum-induced expansion and compression of diaphragm 40 and converts this information into electrical signals, which are sent to controller 66 (FIG. 1) for processing.

Upper wall 82 and side walls 80 of reservoir 30 are substantially thicker than diaphragm 40 (e.g., one-eighth inch thick) to maintain the structural integrity of reservoir 30 during use, as discussed in more detail below. With the exception of diaphragm 40, tube set 20—including reservoir 30 and the various branches 20a, 20b, 20c and fittings (e.g., luers 15, 19, 23, and 28)—is formed as an integral unit from a single piece of material. Put another way, a health care provider or other user of system 10 need not assemble tube set 20 (i.e., interconnect segments 20a–20c, fittings 17, 25, luers 15, 19, 23, and 28, and reservoir 30) before use, or disassemble tube set 20 after use.

In this embodiment, tube set 20 is formed by injection molding. The material used does not depend upon whether tube set 20 is to be used in only one surgical procedure (i.e., disposed of after a single-use) or in multiple procedures. Silicone rubber is a good choice of material because it is autoclavable, elastic (to withstand the pumping action applied to it by pump 26) and biocompatible. Alternatively, tube set 20 may be made from another material which need not be autoclavable, but rather disposable after a single use. In either case, after injection molding, diaphragm 40 is secured to side walls 80 by any suitable sealing technique, e.g., using silicone adhesive.

Figure 4:
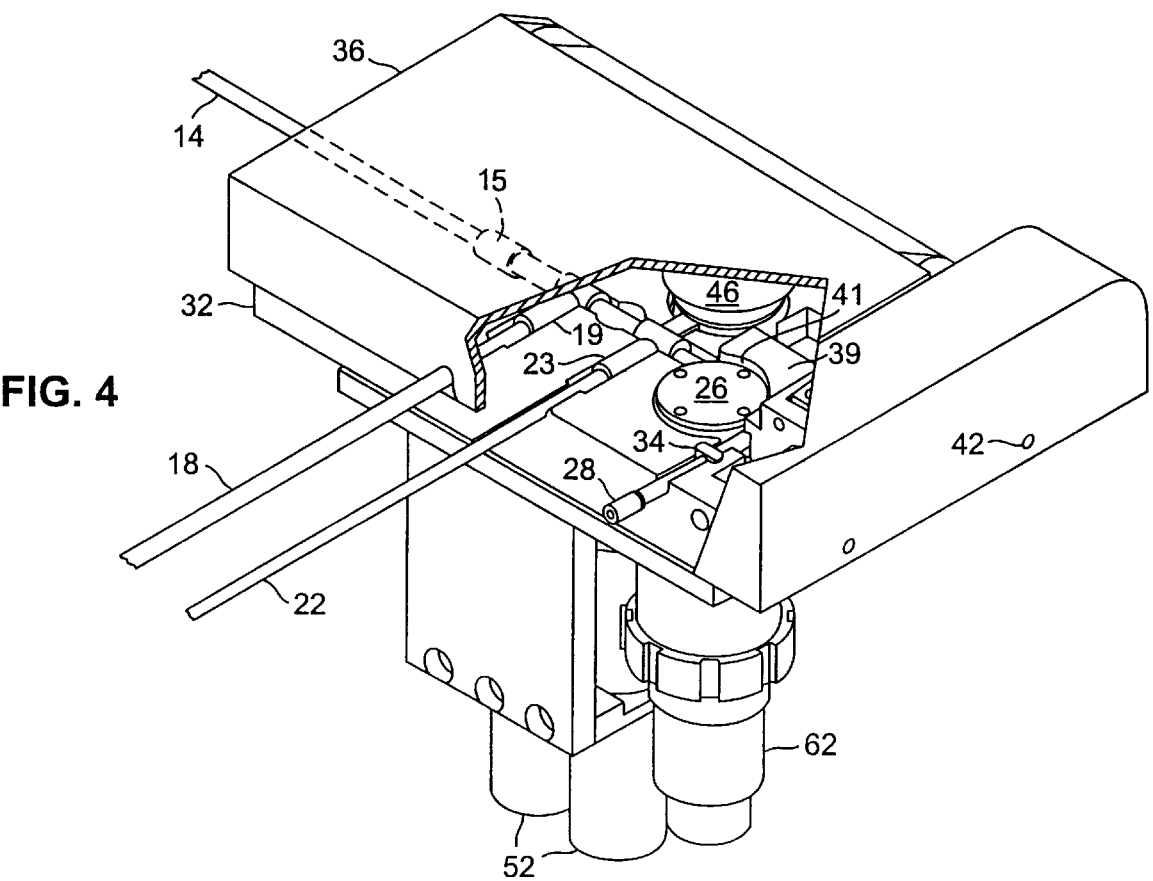
FIG. 4 illustrates the tube set placed within the housing (which is shown closed and partially cut away to expose a portion of the tube set).

As shown in FIGS. 2 and 4, tube set 20 is installed as a unit into a housing 32, which contains peristaltic pump 26 (and motor 62), pinch valves 16, 24 (and their associated plungers 50 and driving solenoids 52), and an electronic transducer 48 for measuring the vacuum level within reservoir chamber 84. An interior channel 72 in housing 32 is sized and shaped to receive the various fittings and branches of tube set 20 for proper positioning. That is, luers 15, 19, 23, and 28 fit snugly within correspondingly-shaped seats in channel 72 so that: (1) reservoir 30 is received by a cylindrical recess 45 of channel 72; (2) tube sections 20a, 20b are located over pinch valve plungers 50; and (3) tube section 20c is wrapped partially around the perimeter of peristaltic pump 26. Note that transducer 48 defines the lower boundary of recess 45 and abuts reservoir diaphragm 40.

The user loads tube set 20 into housing 32 by placing tube set 20 within channel 72 in the orientation discussed above. In addition, a square boss 34 on the exterior of section 20c (and integrally formed with the remainder of tube set 20 during molding) fits into a correspondingly-shaped recess in channel 72 (FIG. 4). Boss 34 helps avoid creeping of tube section 20c in response to the operation of pump 26. Spike line 14 is then attached to tube set 20 at luer 15, and irrigation and aspiration tubes 18 and 22 are attached to tube set 20 at luers 19 and 23. Finally, a drainage tube is connected to luer 28.

After tube set 20 has been loaded, the user closes spring loaded door 36 by pivoting door around hinge 42, and latches door 36 shut (as shown in FIG. 4). In the closed position, door 36 completely covers tube set 20 and secures it in position within housing 32. Closing door 36 also engages several operating features of housing 32. For example, a spring loaded plunger 46 on door 36 engages upper wall 82 of reservoir 30 and firmly urges reservoir 30 (and hence diaphragm 40) against transducer 48 at the lower surface of recess 45. The force of the spring 47 (FIG. 6) is sufficient to create an air-tight seal between the lower periphery of walls 80 and transducer 48. Walls 80, 82 must therefore be sufficiently thick to keep reservoir 30 from being crushed by the spring force.

Closing door 36 also activates a rack and pinion 38 attached to a slidable block 39 of housing 32. In response to rack and pinion 38, block 39 slides toward pump 26 to capture tube set section 20c between pump rollers 27 and a curved peripheral surface 41 of block 39. During operation, as the head of peristaltic pump 26 rotates (clockwise in FIGS. 2 and 4), a set of peripheral rollers 27 alternately compress (against surface 41) and release regions of tube section 20c. This action creates an even flow of fluid through tube set 20 to minimize turbulence in the eye.

Finally, a pair of protrusions 44 located on the underside of door 36 directly opposite pinch valve plungers 50 slightly engage tube set sections 20a, 20b when door 36 is closed. Pinch valves 16, 24 close by compressing tube set sections 20a, 20b against protrusions 44 with plungers 50.

Figure 5:
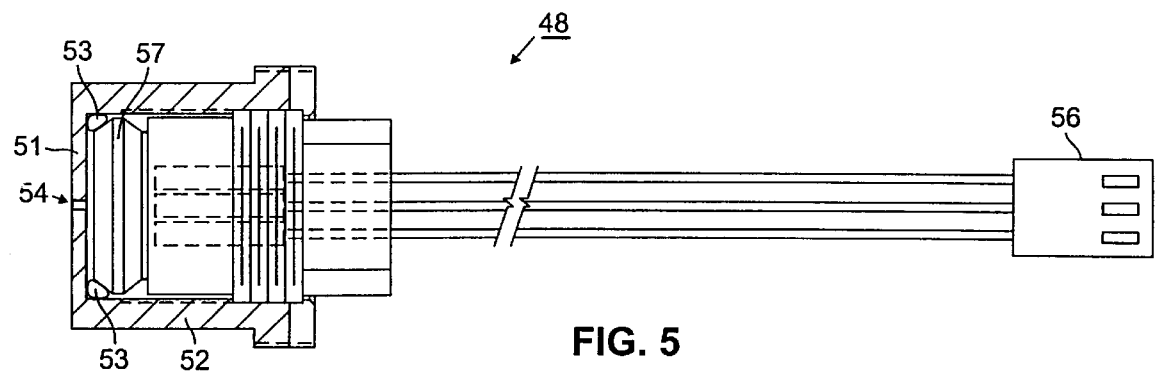
FIG. 5 shows the construction of a pressure sensitive transducer used in the system of FIG. 1.

Referring to FIG. 5, transducer 48 comprises an electronic sensor 57 secured within a cylindrical base 52. Base 52 is secured to the underside of housing 32 so that a circular wall 51 at one end of base 52 defines the lower limit of reservoir recess 45 (FIG. 2). A round hole 54 approximately 1/32 inch in diameter is located at the radial center of wall 51 and is centered over the face of sensor 50 (and also under diaphragm 40 when reservoir 30 is installed). Sensor 57 (commercially available from Motorola) contains a sensing circuit etched on a silicone wafer in the manner of a strain gauge and is mounted on a substrate, which in turn is threaded into an open end of base 52 opposite wall 51 so that the face of sensor 57 abuts the underside of wall 51. Sensor 57 is sealed to base 52 with silicone gel 53.

Figure 6:
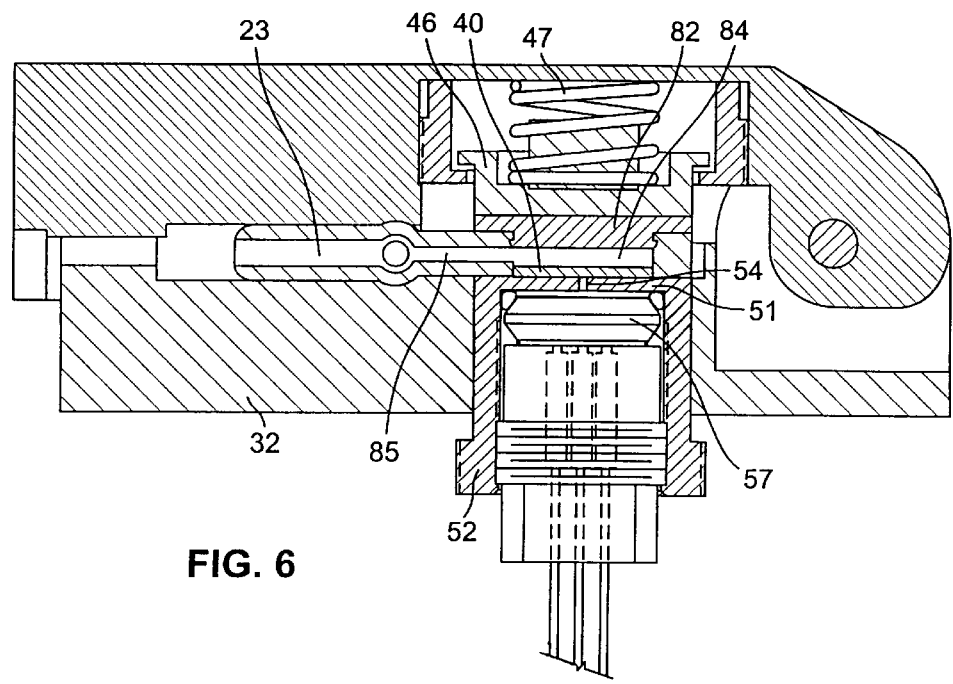
FIG. 6 is a cross-sectional view of the housing illustrating the positioning of the tube set reservoir and the pressure sensitive transducer.

Referring also to FIG. 6, the relative positions of reservoir diaphragm 40 and the components of transducer 48 (when housing 32 is closed) are shown. Spring-loaded plunger 46 urges reservoir 30 firmly against wall 51, thereby creating a tight vacuum seal between diaphragm 40 and wall 51. As a result, vacuum level changes in diaphragm chamber 84 cause diaphragm 40 to expand toward or pull away from wall 51, as the case may be, thereby applying a vacuum force to sensor 57 through hole 54. Sensor 57 serves as an electronic strain gauge, and converts the vacuum forces experienced by diaphragm 40 into electrical signals that are transmitted to controller 66 via connector 56 (FIG. 5).

In operation, prior to the surgical procedure, the user places a sterile tube set 20 in housing 32, attaches the ancillary fluid tubes 14, 18, 22, and closes door 36, all as discussed above. The acceptable range of fluid flow rates and maximum vacuum level are set using controls 68. When the surgical procedure is started, system 10 is "primed" by completely filling tube set 20—including reservoir 30—with irrigation fluid from IV bottle 12. For example, priming is accomplished by repeatedly applying a relatively strong vacuum to tube set 20 several times and allowing fluid to flow into tube set 20. Eliminating air or other gases from reservoir 30 or other parts of tube set 20 increases the response time of system 10 to vacuum changes, as discussed below.

During the surgical procedure, clean irrigating fluid flows into the eye from IV bottle 12, through tube set section 20a (and past pinch valve 16, which is opened by controller 66), and through irrigation line 18. (Pinch valve 24 is normally closed by controller 66, as will be explained.) Controller 66 operates pump 26 (via motor 62) to continuously aspirate fluid from the eye (via line 22 and tube set section 20c) into drainage. Increasing the speed of pump 26 increases the vacuum applied to tube set 20, thereby withdrawing fluid from the eye at a faster rate. Conversely, reducing the speed of pump 26 lowers the vacuum applied to tube set 20, and thus slows the aspiration rate.

Transducer 48 measures the vacuum created in tube set 20 via reservoir diaphragm 40, as discussed above. Due to its location at the junction of aspiration tube 22 and tube set section 20c, reservoir 30 receives the aspirated fluid directly from the eye. Because reservoir 30 is completely filled with fluid during the priming procedure, changes in vacuum level rapidly induce corresponding deflections of reservoir diaphragm 40, causing diaphragm 40 to attempt to expand (as the vacuum level decreases) and contract (in response to increasing vacuum levels within tube set 20).

The thickness, diameter and material of reservoir diaphragm 40 provides a one-to-one correspondence between the vacuum level in reservoir 30 and the deflection of diaphragm 40 within a range from 0 mm Hg–500 mm Hg.

Sensor 57 converts the vacuum forces generated by diaphragm 40 into corresponding electrical signals that represent the vacuum level within reservoir 30. Controller 66 uses these signals to determine whether the speed of pump 26 should be increased or decreased to maintain the flow rate of within the preset range and the vacuum level in tube set 20 below the preset maximum.

Specifically, controller 66 responds to decreases in the flow rate, as indicated by the detected vacuum level, by increasing the speed of pump 26 to increase the vacuum applied to tube set 20 and withdraw fluid from the eye at a greater rate. Conversely, as flow rate increases (as indicated by an increase in the vacuum applied by diaphragm 40 to sensor 57), controller 66 slows pump 26, thereby maintaining the flow rate within the desired range.

If a sudden event (such as clogging of the surgical instrument) occurs which causes the vacuum level measured by transducer 48 to increase rapidly, controller 66 opens pinch valve 24, to reduce the vacuum level in tube set 20 to zero. This avoids damage which would otherwise occur if intraocular pressure were allowed to build unchecked.

When the surgical procedure has been completed, tube set 20 (including reservoir 30) is removed from housing 32 as single unit by simply detaching tube set 20 from external lines 14, 18, 22 and drainage. Tube set 20 is then either discarded or sterilized for use with a subsequent patient. In any event, system 10 is readied for use with a subsequent patient by simply installing another (or a resterilized) tube set 20 as a unit in housing 32.

Reservoir diaphragm 40 provides a sealed interface between the aspirated fluid in reservoir 30 and transducer 48. Accordingly, fluid aspirated from the patient's eye is isolated from transducer 48. Among other advantages, contamination (and potential fouling) of transducer 48 is avoided, as is so-called "cross-contamination" (i.e., exposing a subsequent patient to fluids aspirated from a previous patient on whom system 10 was used).

Other embodiments are within the scope of the following claims.

For example, reservoir 30 and diaphragm 40 may be manufactured as a single, integral unit from a unitary piece of material. That is, diaphragm 40 may be formed at the same time that the remainder of reservoir 30 is fabricated, thereby eliminating the need for a separate attachment step.

Reservoir 30 may be detachable from the remainder of tube set 20, rather than being integrally formed with it.

What is claimed is:

1. Apparatus for use in eye surgery, comprising
   a tube set through which fluid is supplied to and withdrawn from the eye, said tube set including a fluid reservoir having a diaphragm disposed thereon that deflects in response to a vacuum level in said reservoir,
   a housing configured to receive said tube set, said housing including a door movable between an open position to allow said tube set to be installed in and removed from said housing and a closed position in which said tube set is retained in said housing, and
   a sensor mounted on said housing for detecting deflections of said diaphragm,
   wherein said housing further comprises a spring-biased plunger for urging said reservoir into a recess in said housing adjacent to said sensor when said door is in the closed position.

2. The apparatus of claim 1 wherein said reservoir and said diaphragm are configured so that a surface of said diaphragm that is exposed to fluid in said reservoir from said tube set is in contact with the fluid over substantially all of an area of said surface.

3. The apparatus of claim 2 wherein said reservoir is configured to be substantially filled with fluid from said tube set.

4. The apparatus of claim 1 wherein said tube set is constructed as an integral unit from a single piece of material.

5. The apparatus of claim 4 wherein said material comprises plastic.

6. The apparatus of claim 4 wherein said material comprises silicone rubber.

7. The apparatus of claim 1 wherein said diaphragm has a thickness selected to deflect in said selected manner in response to the vacuum level in said tube set.

8. The apparatus of claim 7 wherein said thickness is selected so that said diaphragm deflects linearly over a pressure range of 0 mm Hg to 500 mm Hg.

9. The apparatus of claim 7 wherein said diaphragm has a thickness in the range of 0.005 inches to 0.006 inches.

10. The apparatus of claim 1 wherein said diaphragm includes silicone rubber.

11. The apparatus of claim 1 wherein said sensor and said diaphragm are disposed adjacent to opposite sides of a surface of said recess adjacent to said sensor, and further comprising an opening in said surface between said opposite sides.

12. The apparatus of claim 1 wherein said sensor is constructed to produce electrical signals representing the vacuum level in said reservoir in response to deflections of said diaphragm, and further comprising a controller for controlling a rate at which fluid is withdrawn from the eye based on said electrical signals.

13. The apparatus of claim 1 further comprising a pump disposed to engage said tube set to induce said vacuum and withdraw the fluid from the eye, said controller adjusting a speed of said pump in response to said signals produced by said sensor.

14. The apparatus of claim 13 wherein said pump is a peristaltic pump.

15. The apparatus of claim 1 further comprising
    a peristaltic pump mounted on said housing and disposed to engage said tube set to induce said vacuum and withdraw the fluid from the eye, and
    a mechanism for urging a section of said tube set against said peristaltic pump when said door is in the closed position, and releasing said section of said tube from said pump when said door is in the open position.

16. The apparatus of claim 1 wherein said tube set includes a first portion configured to receive the fluid from a supply and couple the supplied fluid to the eye and a second portion configured to receive fluid withdrawn from the eye and couple the withdrawn fluid to drainage.

17. The apparatus of claim 16 further comprising a branch that interconnects said first portion and said second portion.

18. The apparatus of claim 16 wherein said tube set is formed by injection molding.

* * * * *

UNITED STATES PATENT AND TRADEMARK OFFICE
CERTIFICATE OF CORRECTION

PATENT NO.   : 5,910,110
DATED        : June 8, 1999
INVENTOR(S)  : David Bastable It is certified that error appears in the above-identified patent and that said Letters Patent is hereby corrected as shown below:

Col. 5, line 36, replace "50" with --57--.

Col. 8, claim 13, line 20, replace "1" with --12--.

Signed and Sealed this

Fourteenth Day of December, 1999

Attest:

Attesting Officer

Q. TODD DICKINSON

Acting Commissioner of Patents and Trademarks